United States Patent [19]

Young

[11] Patent Number: 5,509,919
[45] Date of Patent: Apr. 23, 1996

[54] APPARATUS FOR GUIDING A REAMING INSTRUMENT

[76] Inventor: Merry A. Young, 540 N. Mulford, #2, Rockford, Ill. 61107

[21] Appl. No.: 125,690

[22] Filed: Sep. 24, 1993

[51] Int. Cl.⁶ .................................................. A61B 17/56
[52] U.S. Cl. .............................. 606/80; 606/96; 606/102
[58] Field of Search ........................... 606/63, 62, 64, 606/60, 67, 68, 72, 80, 84, 85, 86, 95, 96, 99, 102, 104

[56] References Cited

U.S. PATENT DOCUMENTS

| | | | |
|---|---|---|---|
| 2,821,979 | 2/1958 | Cameron | 606/64 |
| 3,530,854 | 9/1970 | Kearney. | |
| 3,760,802 | 9/1973 | Fischer et al. | 606/63 |
| 3,779,239 | 12/1973 | Fischer et al. | 606/63 |
| 4,204,531 | 5/1980 | Aginsky | 606/63 |
| 4,275,717 | 6/1981 | Bolesky | 606/63 |
| 4,453,539 | 6/1984 | Raftopoulos et al. | 606/63 |
| 4,705,032 | 11/1987 | Keller | 606/62 |
| 4,721,103 | 1/1988 | Freedland | 606/63 |
| 4,800,873 | 1/1989 | Audell. | |
| 4,805,607 | 2/1989 | Engelhardt et al. | 606/67 |
| 4,919,673 | 4/1990 | Willert et al. | 623/23 |
| 5,002,543 | 3/1991 | Bradshaw et al. | 606/62 |
| 5,057,103 | 10/1991 | Davis | 606/63 |
| 5,078,746 | 1/1992 | Garner | 623/16 |
| 5,102,413 | 4/1992 | Poddar | 606/62 |
| 5,122,146 | 6/1992 | Chapman et al. | 606/102 |
| 5,171,248 | 12/1992 | Ellis | 606/102 |
| 5,174,302 | 12/1992 | Palmer | 128/772 |
| 5,234,435 | 8/1993 | Seagrave, Jr. | 606/103 |

FOREIGN PATENT DOCUMENTS 2484243  12/1981  France ...................................... 606/63

OTHER PUBLICATIONS

Brochure, Synthes®, Aug. 1992, pages showing instruments for fracture reduction. 3 pages, Author unknown.

Primary Examiner—Stephen C. Pellegrino
Assistant Examiner—Guy V. Tucker
Attorney, Agent, or Firm—Poms, Smith, Lande & Rose

[57] ABSTRACT

A method and apparatus useful in the reduction of a bone fracture is disclosed and relates to a guide rod inserted into a medullary canal of a bone. The guide rod includes a retention mechanism that holds the guide rod in place during the bone reduction procedure. The retention mechanism may include a finger member that contacts material within the bone to hold the guide rod in place.

11 Claims, 12 Drawing Sheets

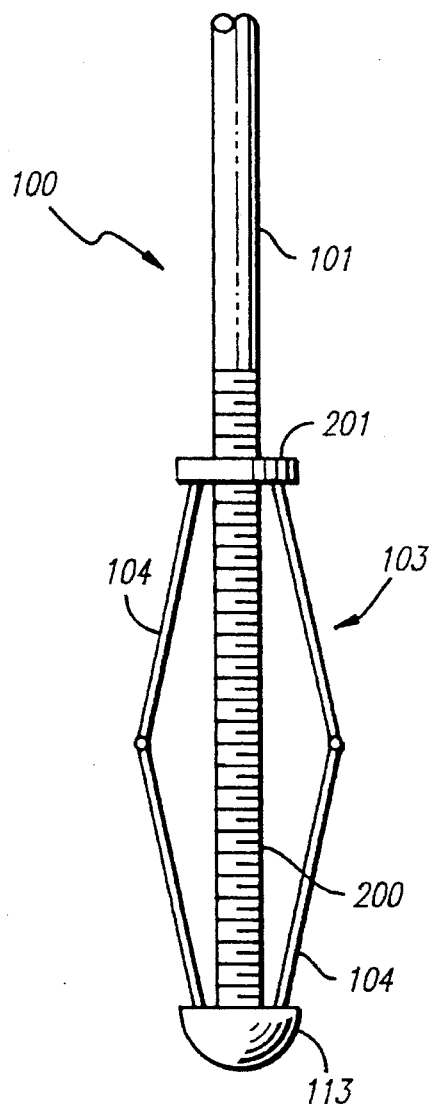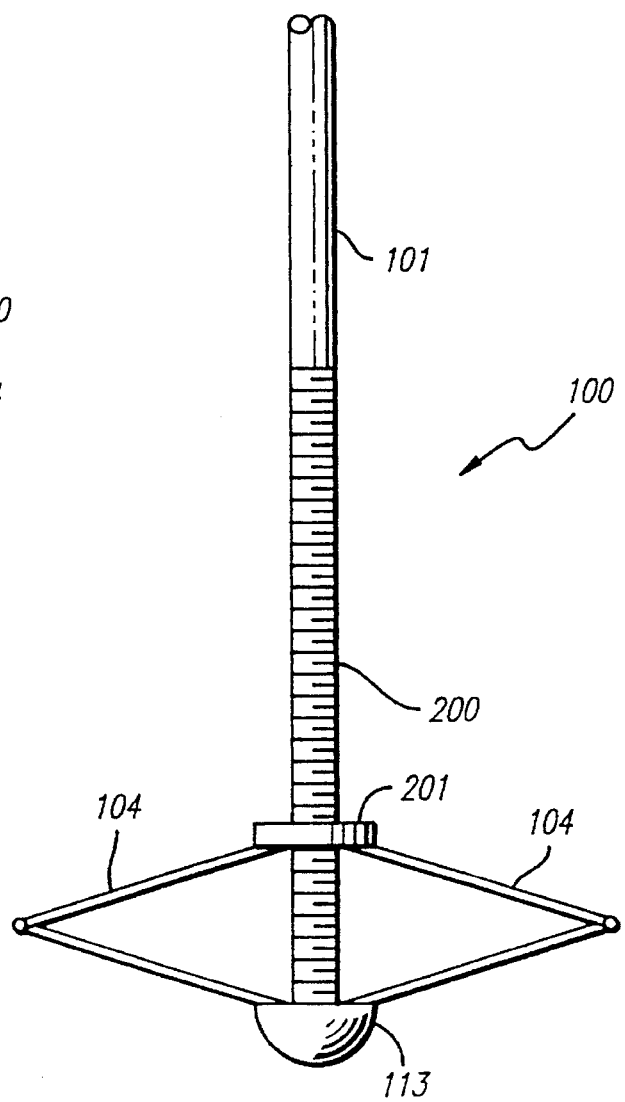
FIG. 2A
FIG. 2B

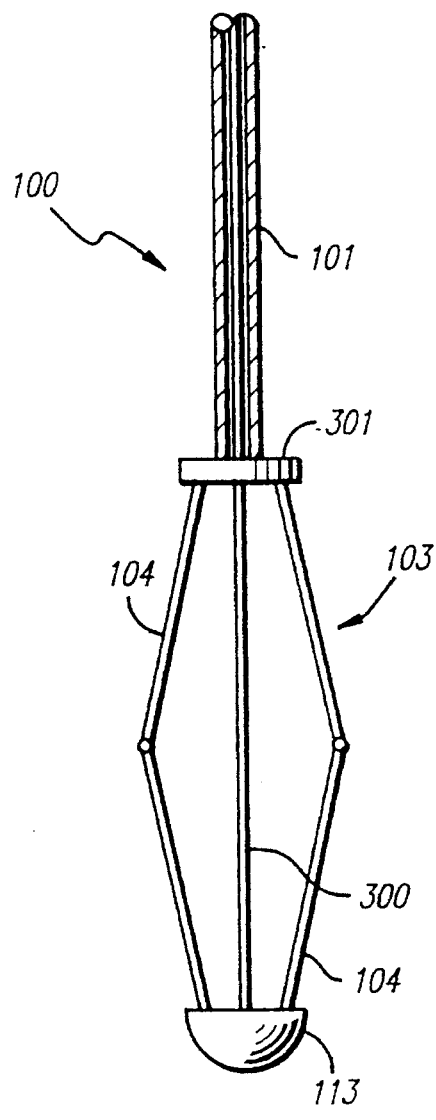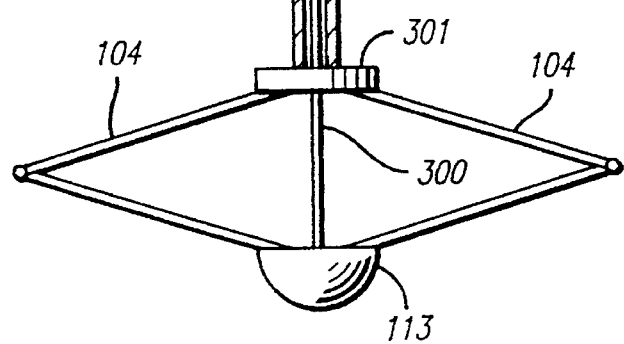
FIG. 3A
FIG. 3B

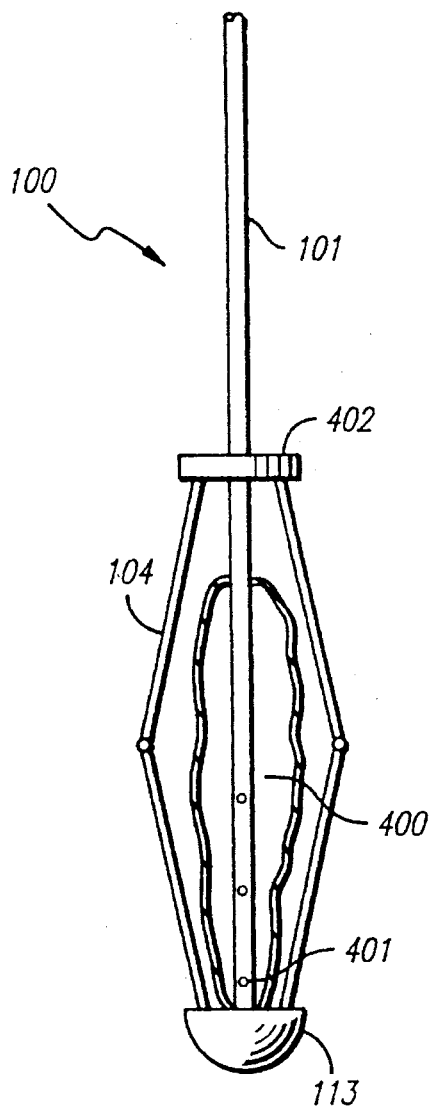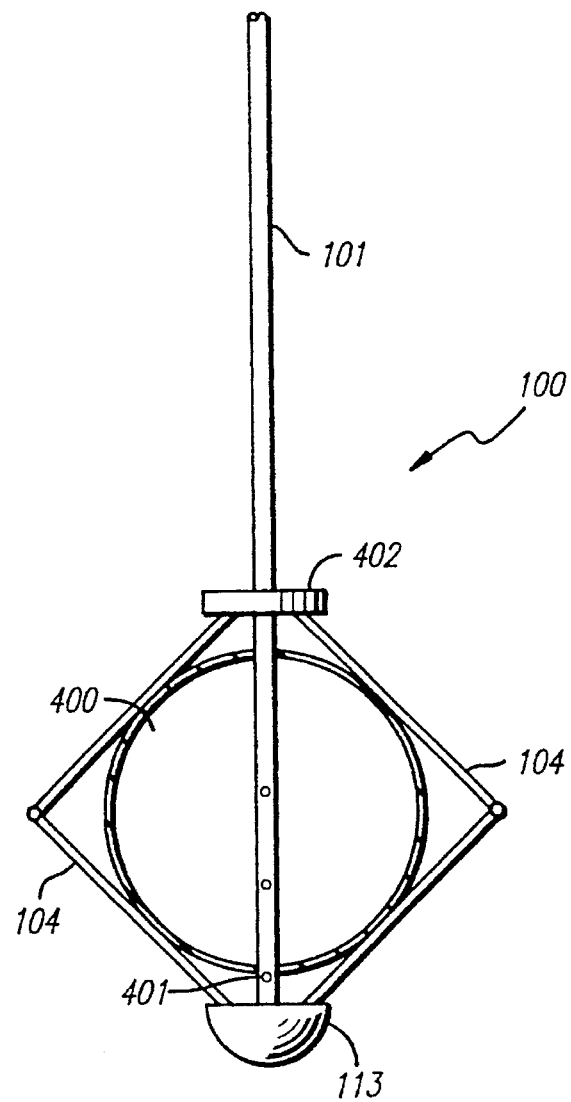
FIG. 4A
FIG. 4B

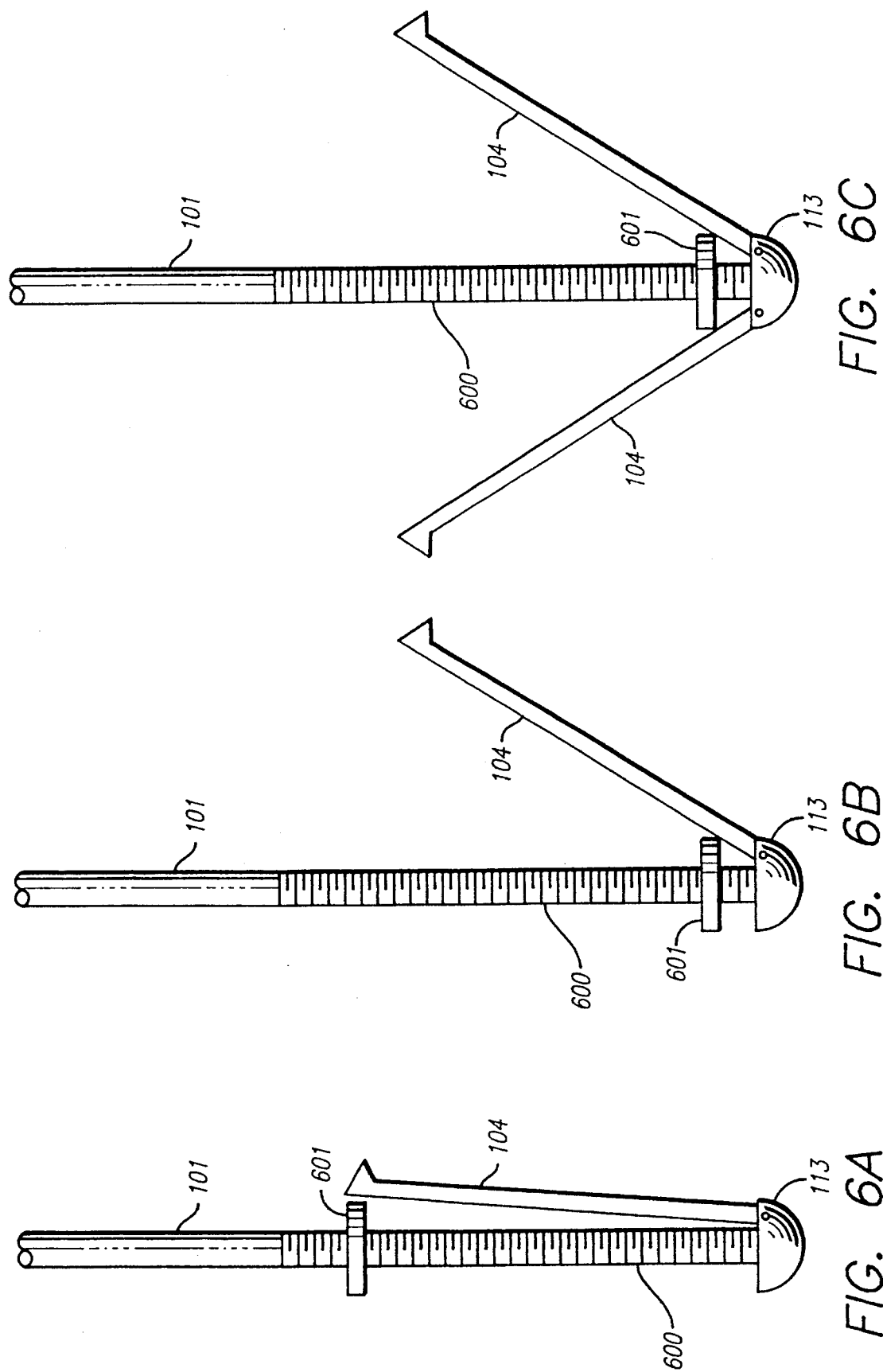

APPARATUS FOR GUIDING A REAMING INSTRUMENT

FIELD OF THE INVENTION

The present invention generally relates to a method and apparatus for reducing the fracture of a bone and particularly to a method and apparatus for holding a guide rod in place in a medullary canal of a bone during reduction of a fracture in that bone.

BACKGROUND OF THE INVENTION

Prior to setting a bone fracture, the fracture must be reduced. That is, the various bone fragments or pieces must be repositioned in their proper relative arrangement before the fractured bone can be fixed or stabilized for healing.

Various techniques exist for reducing bone fractures, one of which is disclosed in U.S. Pat. No. 5,122,146. In that patent, the fracture is reduced using, in part, a fracture reduction tool and a "guide wire". Through manipulation of the fracture reduction tool (and the help of an assistant if necessary), proper alignment of the fragments is achieved. The proper alignment is then maintained by the insertion of the guide wire through the medullary canal of each fragment.

Further reduction and preparation for stabilization is performed by reaming the medullary canal of the fragments that are now held in alignment. This operation is achieved by sequentially advancing and retracting a series of hollow reaming instruments over the guide rod. With the use of each successive reaming instrument, the medullary canal is increased in size until it is enlarged sufficiently to receive a nail or pin that will permanently keep the bone fragments in proper alignment and thereby stabilize the bone for healing.

Although not mentioned in U.S. Pat. No. 5,122,146, in practice, the use of a guide wire in the reduction of fractures can prove highly disruptive. Most frequently this occurs during the reaming operation where the reaming instruments are being advanced and retracted over the guide wire.

Since the guide wire is not secured in position within the medullary canal during the reaming operation, retraction of the hollow reaming instrument, through contact with the guide wire, often pulls the guide wire out of position, even when the surgeon is using extreme caution. When this occurs, the entire reduction procedure must be started again thus obviously leading to greater risk of damaging the fractured area as well as increasing the time required to complete the procedure.

No guide wires of the known prior art have provided any acceptable solution to this problem. The guide wire of U.S. Pat. No. 5,122,146 includes a bead-tip at its distal end, however the function of the bead-tip is primarily to prevent the reaming instrument from being advanced too far within the medullary canal; it does not secure the guide wire within the canal.

SUMMARY OF THE INVENTION

It is therefore the goal of the present invention to overcome the problems associated with the use of a guide wire, guide rod or the like in the procedure of reducing fractures. Particularly, it is the goal of the present invention to provide a method and apparatus capable of ensuring that a guide wire (or guide rod or the like) is secured in a desired position in the medullary canal of the fractured bone throughout the reduction procedure.

The various novel features of the invention which are believed to achieve these goals as well as to provide other advantages and improvements will be understood from the following specification and accompanying drawings in which a preferred embodiment of the invention is illustrated by way of example. It is expressly understood, however, that the specification and drawings are for purposes of description and illustration only and are not intended as a definition of the limits of the invention as set forth in the claims.

BRIEF DESCRIPTION OF THE DRAWINGS

FIGS. 2A–2B illustrate a second embodiment of a guide rod in accordance with the present invention;

FIGS. 3A–3B illustrate a third embodiment of a guide rod in accordance with the present invention;

FIGS. 4A–4B illustrate a fourth embodiment of a guide rod in accordance with the present invention;

FIGS. 6A–6C illustrate a sixth embodiment of a guide rod in accordance with the present invention;

DETAILED DESCRIPTION

Figure 1:
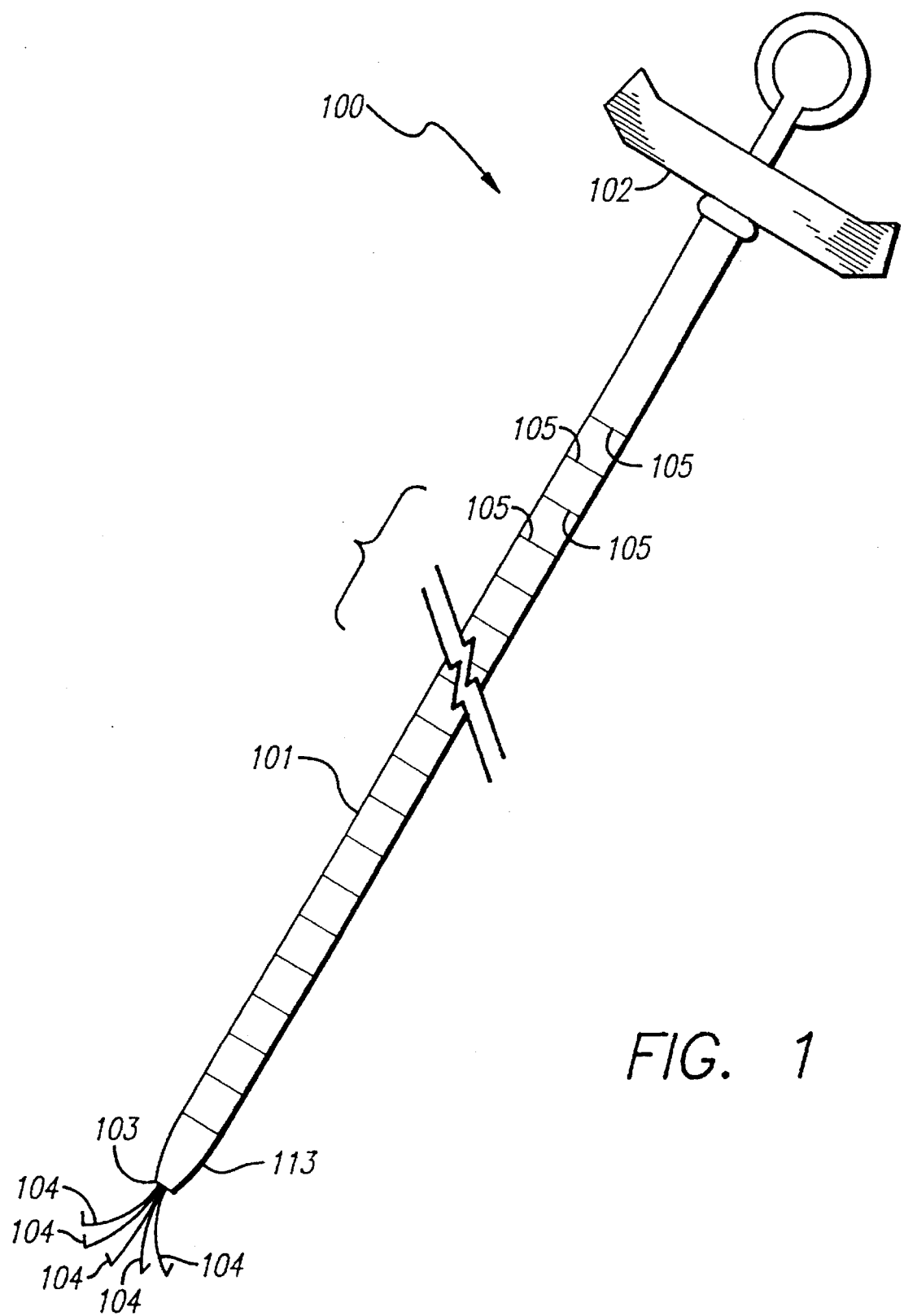
FIG. 1 is a plan view of a guide rod in accordance with an embodiment of the present invention.

A guide rod 100 in accordance with the present invention is depicted in FIG. 1 and includes an elongated rod section 101 which is substantially circular in cross-section. The rod section 101 may be made of a flexible material so that the guide rod 100 may be used in reducing fractures that are either substantially straight or that have a degree of curvature. Provided at regular intervals along the length of the elongated rod section are radiopaque measuring markers 105 that are useful for monitoring the location of the rod within the medullary canal. Finally, the distal end 113 of the elongated rod section 101 is formed to have a bullet shape. This shape provides advantages over other shapes such as beaded ends or blunt shapes as it facilitates advancement of the guide rod 100 through the material within the medullary canal of the bone.

At the proximal end of the guide rod 100 is a handle arrangement 102 that is gripped by the user and used to facilitate insertion of the guide rod into the medullary canal of a bone. Once the guide rod 100 is in place, the handle arrangement may be removed in order to allow further steps in the fracture reducing procedure.

At the distal end of the guide rod 100 is a guide rod retention device 103 for retaining the guide rod 100 in place once it has been moved into a desired position within the medullary canal of the bone. The retention device includes a plurality of finger members 104 that are selectively actuatable between a first position where each finger member 104 rests substantially within the cross-sectional profile of the guide rod 100 (not shown) and a second position where each finger member 104 extends flares outwardly from the cross-sectional profile of the guide rod 100. When in the second position, the finger members 104 come into contact with material within the bone and thereby anchor the guide rod in the desired position within the medullary canal.

It will be appreciated that any number of mechanisms may be incorporated into the guide rod 100 to provide the actuating function for the finger members 104. In one embodiment, that mechanism may include a screw-type device similar to that used in a rotary actuated ballpoint pen. By turning the handle assembly 102, the finger members 104 emerge from the distal end and spread outwardly to contact material within the bone. Other contemplated embodiments might use a tension notch device similar to that of a floor jack or a pressurized trigger device similar to that used to actuate a balloon-tip catheter.

Instead of being actuated through the distal end of the guide rod 100 as depicted in FIG. 1, it is contemplated the finger members 104 may be actuated outwardly from the cross-sectional profile of the guide rod 100 as depicted in FIGS. 2–7. Finger members 104 actuated in this manner may initially rest completely within the cross-sectional profile or may rest adjacent to the cross-sectional profile. A number of different ways may be implemented to actuate the finger members 104 in this manner.

Referring to FIGS. 2A and 2B, the finger members 104 extend between the distal end 113 of the guide rod 101 and a threaded nut member 201 that is mounted on corresponding threads 200 on the guide rod. By rotating the nut member 201 through the handle assembly 102, the finger members 104 begin bulging outwardly from the cross-sectional profile of the guide rod 100 as seen in FIG. 2B so as to come into contact with material within the bone.

Referring to FIGS. 3A and 3B, the finger members 104 extend between the distal end 113 of the guide rod 100 and a sealing ring 301 such as an O-ring that is mounted on an actuating shaft 300 that extends through the guide rod 100 and is attached to the distal end 113. By urging the actuating shaft 300 upwardly through the guide rod 100, the finger members 104 begin bulging outwardly from the cross-sectional profile of the guide rod 100 as seen in FIG. 3B so as to come into contact with material within the bone. It is contemplated that the shaft 300 could be locked in place using a locking mechanism similar to that used in a push-button ballpoint pen or to that used in an umbrella.

Referring to FIGS. 4A and 4B, the finger members 104 extend between the distal end 113 of the guide rod 100 and a ring 402 that is slidably mounted on the guide rod 100. Mounted on the guide rod 100 between the ring 402 and the distal end 113 is a bladder 400 that is inflatable through air holes 401 located in the guide rod 100. Upon inflation of the bladder 400, the finger members 104 begin bulging outwardly from the cross-sectional profile of the guide rod 100 as seen in FIG. 4B so as to come into contact with the material within the bone.

Figure 5A:
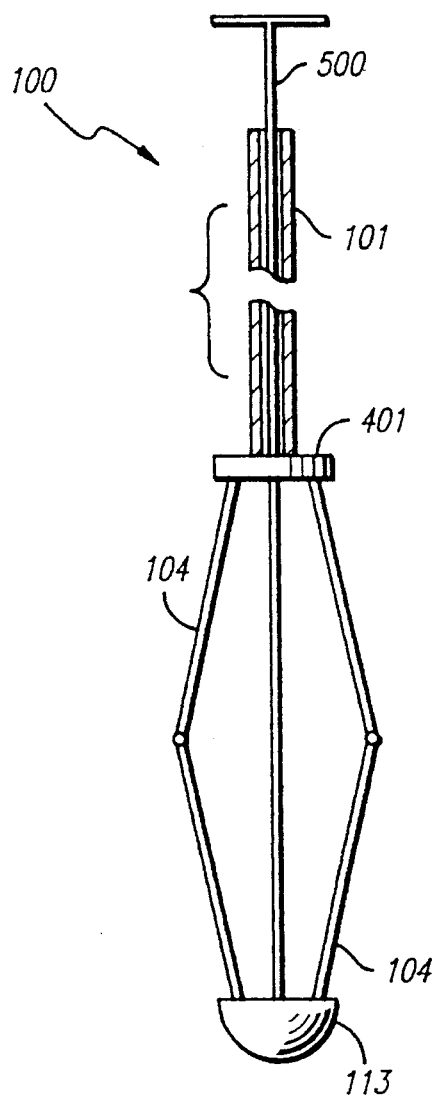
FIGS. 5A–5B illustrate a fifth embodiment of a guide rod in accordance with the present invention.
Figure 5B:
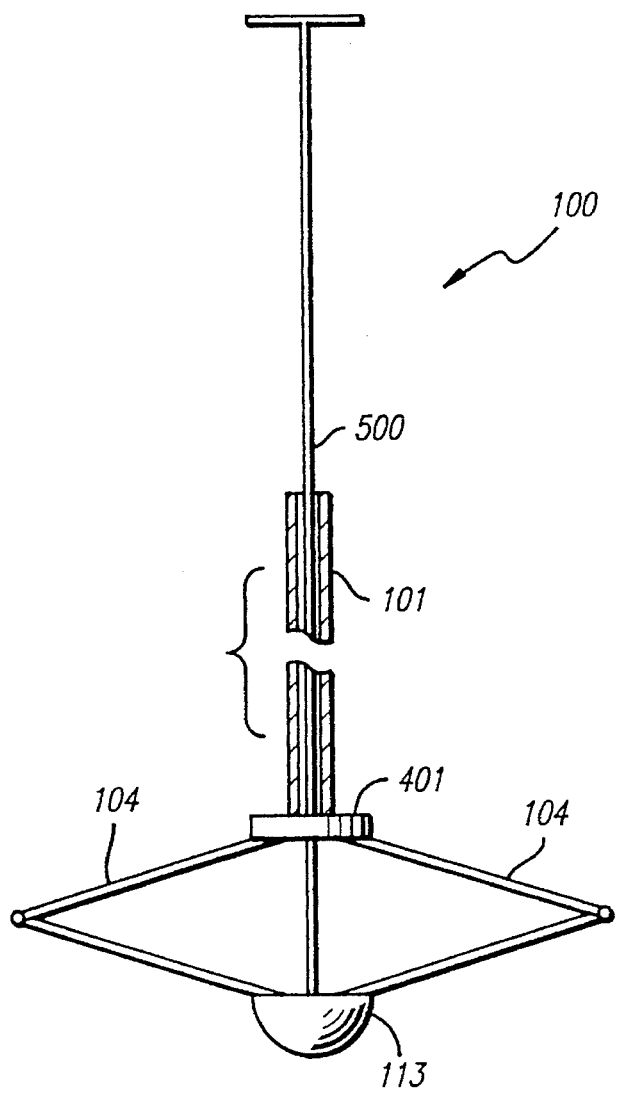

Referring to FIGS. 5A and 5B, the finger members 104 extend between the distal end 113 of the guide rod and the end elongated shaft 101 of the guide rod 100. An actuating wire 500 extends through the shaft 101 and is connected to the distal end 113 of the guide rod 100. By urging the wire 500 upwardly through the guide rod 100, the finger members 104 begin bulging outwardly from the cross-sectional profile of the guide rod 100 as seen in FIG. 5B so as to come into contact with the material within the bone.

Referring to FIGS. 6A and 6B, a finger member 104 is pivotally attached to the distal end 113 of the guide rod 100. A threaded nut 601 is mounted on the guide rod 100 through corresponding threads 600 on the guide rod 100. As the nut 601 is threaded downwardly towards the distal end of the guide rod 100, the body of the nut 601 forces the finger member 104 to pivot such that a pointed end of the finger member 104 is urged outwardly from the cross-sectional profile of the guide rod 100 as seen in FIG. 6B so as to come into contact with the material within the bone. Of course, a plurality of finger members 104 may be utilized as depicted in FIG. 6C.

Figure 7A:
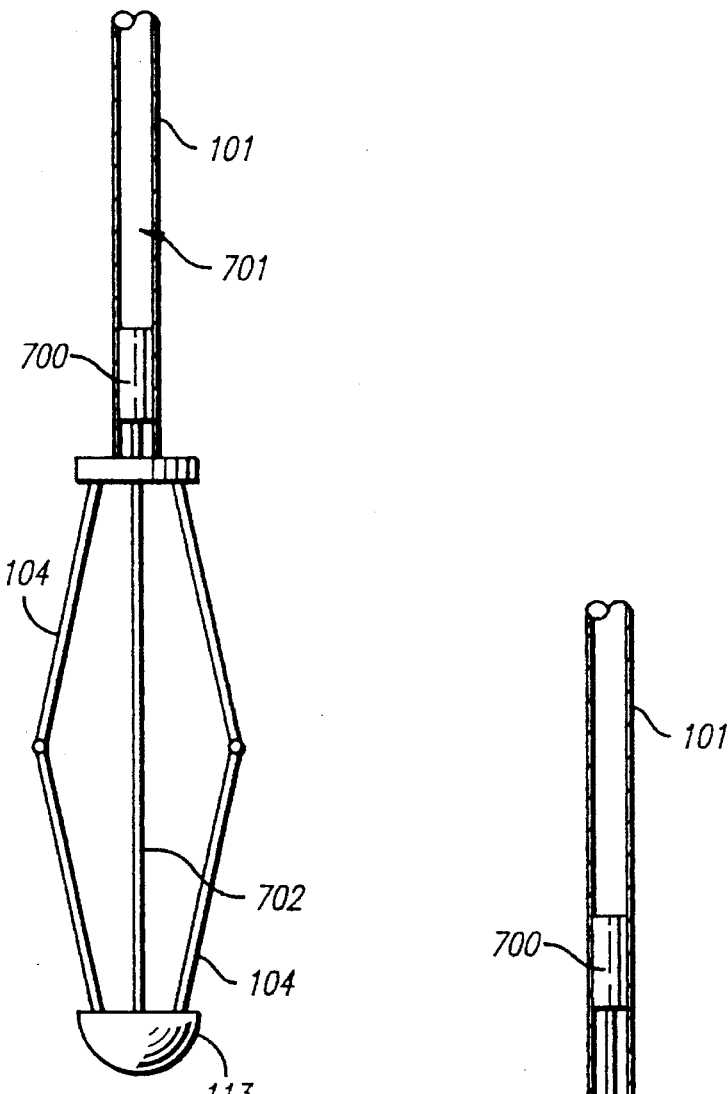
FIGS. 7A–7B illustrate a seventh embodiment of a guide rod in accordance with the present invention.
Figure 7B:
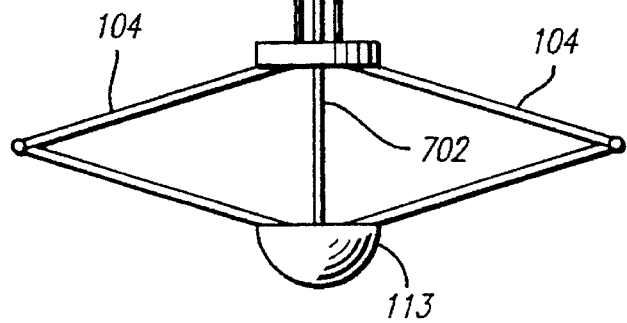

Referring to FIGS. 7A and 7B, the finger members 104 extend between the distal end 113 of the guide rod 100 and the end of the elongated rod 101 of the guide rod 100. The inside of the elongated rod 101 serves as a hydraulic cylinder housing 701 for a hydraulic piston arrangement 700 that is connected to the distal end 113 of the guide rod 100. By introducing and withdrawing fluid into and out of the cylinder housing 701, the finger members 104 are actuated. When fluid is withdrawn, the distal end 113 of the guide rod 100 is urged upwardly and the finger members 104 are urged outwardly from the cross-sectional profile of the guide rod 100 as seen in FIG. 7B so as to come into contact with the material within the bone.

Referring now to FIGS. 8–12, the use of the guide rod 100 in the reduction of a fractured femur is described. Initially, of course, the patient has been anesthetized and an incision has been made to allow insertion of various tools into the fractured area.

Figure 8:
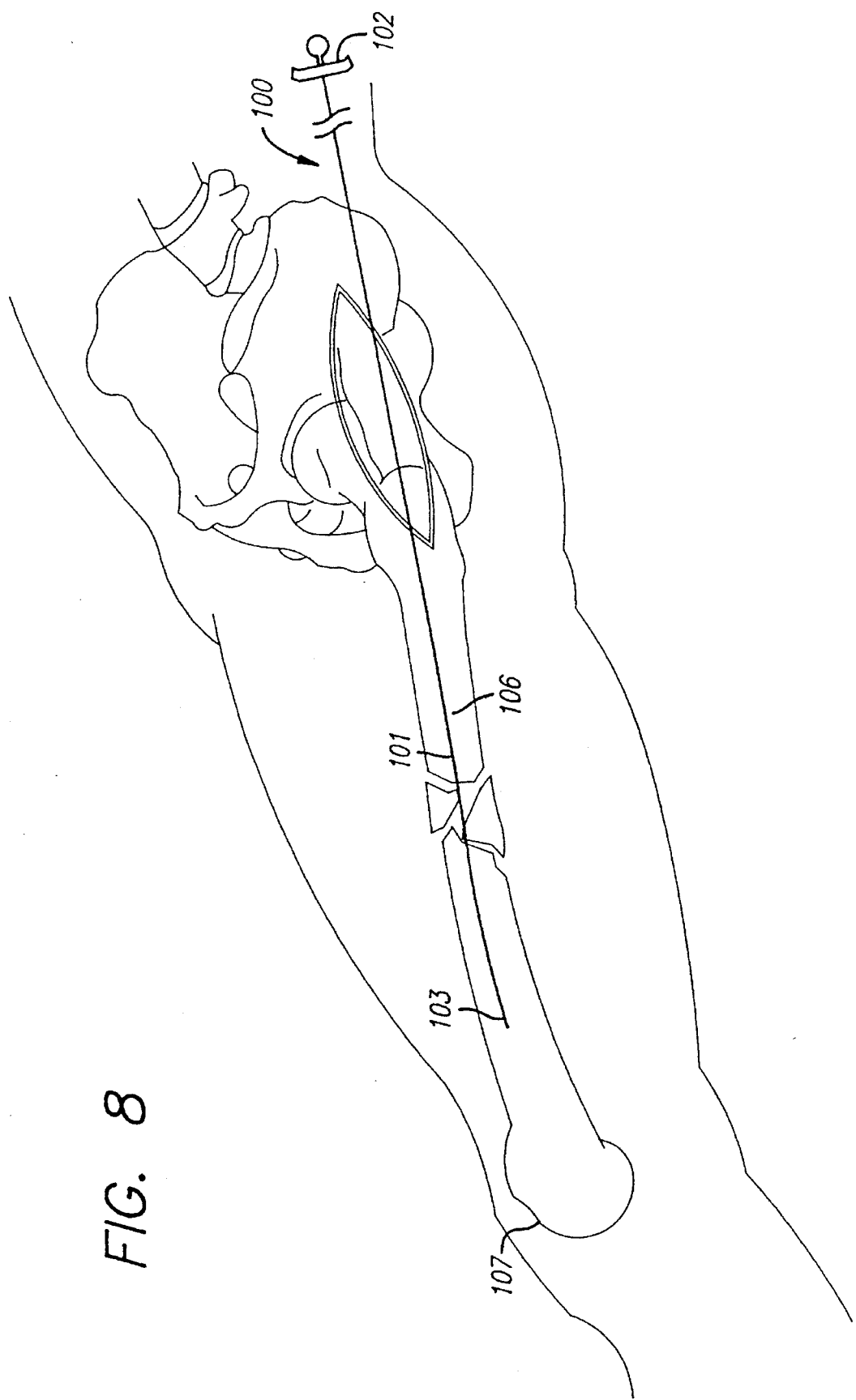
FIG. 8 illustrates the positioning of a guide rod in accordance with an embodiment of the present invention within the medullary canal of a fractured femur.

As shown in FIG. 8, the guide rod 100 is introduced into the medullary canal 106 of the fractured bone and advanced towards the joint 107 of the bone. During this insertion and advancement step of the reduction procedure, the finger members 104 of the retention mechanism 103 are kept within the circular cross-sectional profile of the guide rod 100, that is, the retention mechanism 103 is unactuated.

Figure 9:
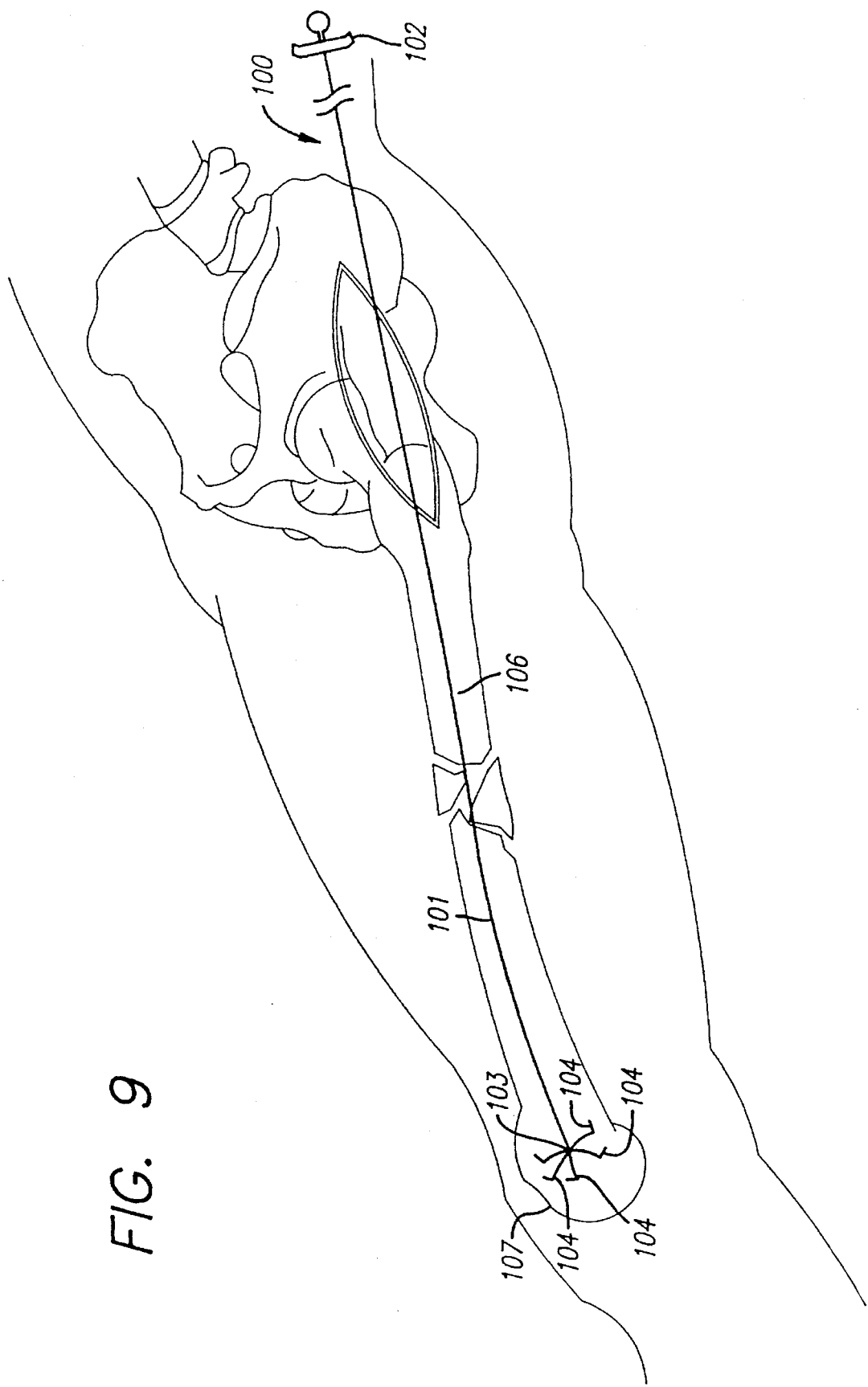
FIG. 9 illustrates the secured position of a guide rod in accordance with an embodiment of the present invention within the medullary canal of a fractured femur.

Once the guide rod 100 is located in the desired position, the retention mechanism 103 is actuated by turning the handle assembly 102. This leads to the flaring finger members 104, extending outwardly from the cross-sectional profile of the guide rod section 101 and contacting material within the joint area 107 of the fractured bone and thereby anchoring the guide rod 100 into place as shown in FIG. 9.

Figure 10:
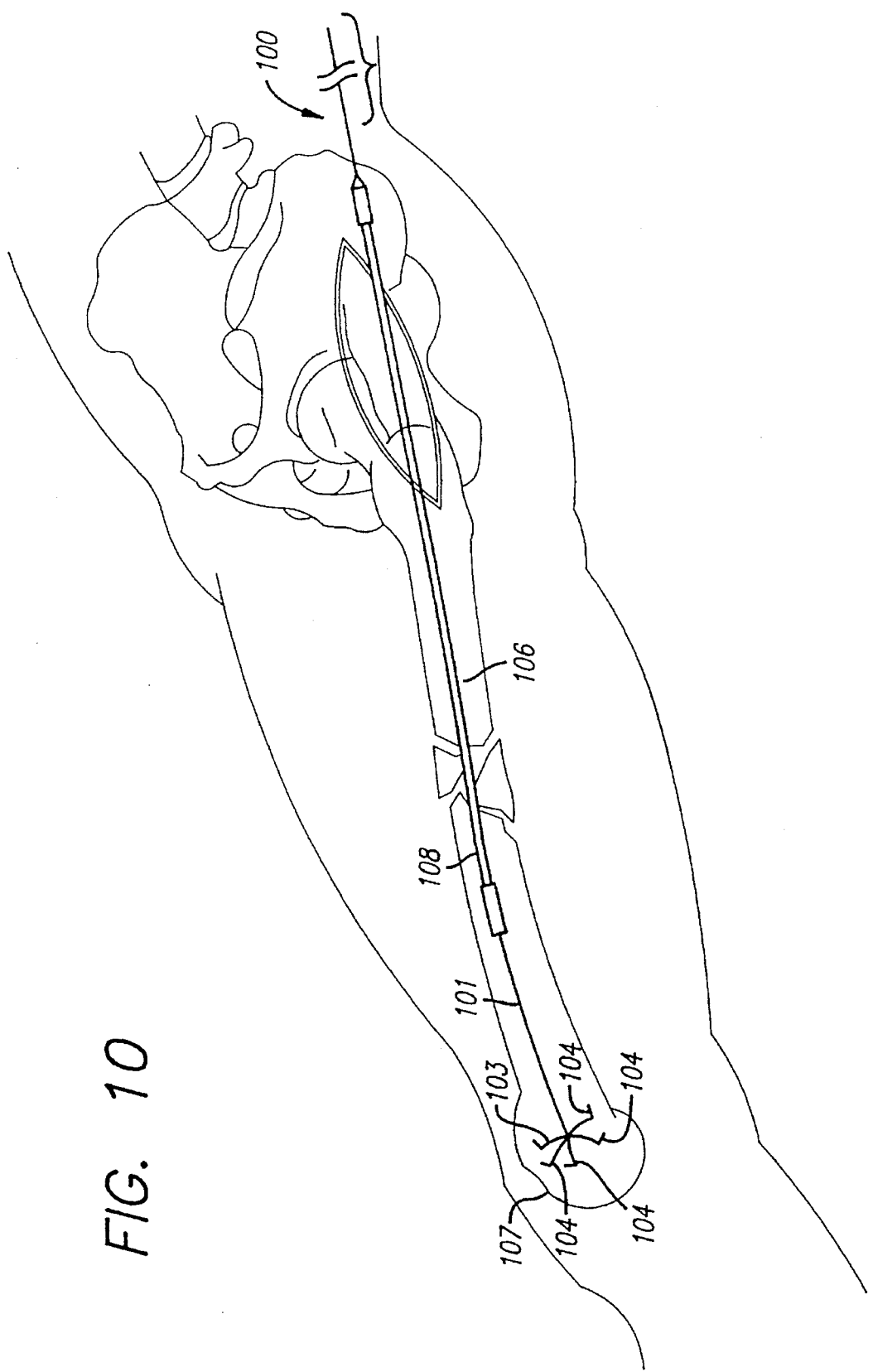
FIG. 10 illustrates the advancement of a reaming instrument guided by a guide rod in accordance with an embodiment of the present invention.

The guide rod 100 thus being anchored into place, the surgeon may then begin the reaming stage of the procedure to prepare the medullary canal 106 for receiving a permanent nail or rod 109 that will stabilize the fracture for healing. The finger members 104 are locked into place and the handle arrangement 102 is then removed. A series of hollow reaming instruments 108 are then sequentially advanced and retracted along the guide rod 100, the guide rod 100 having a diameter that is insertable into the hollow of each reaming instrument 108. FIG. 10 illustrates the reaming operation.

Figure 11:
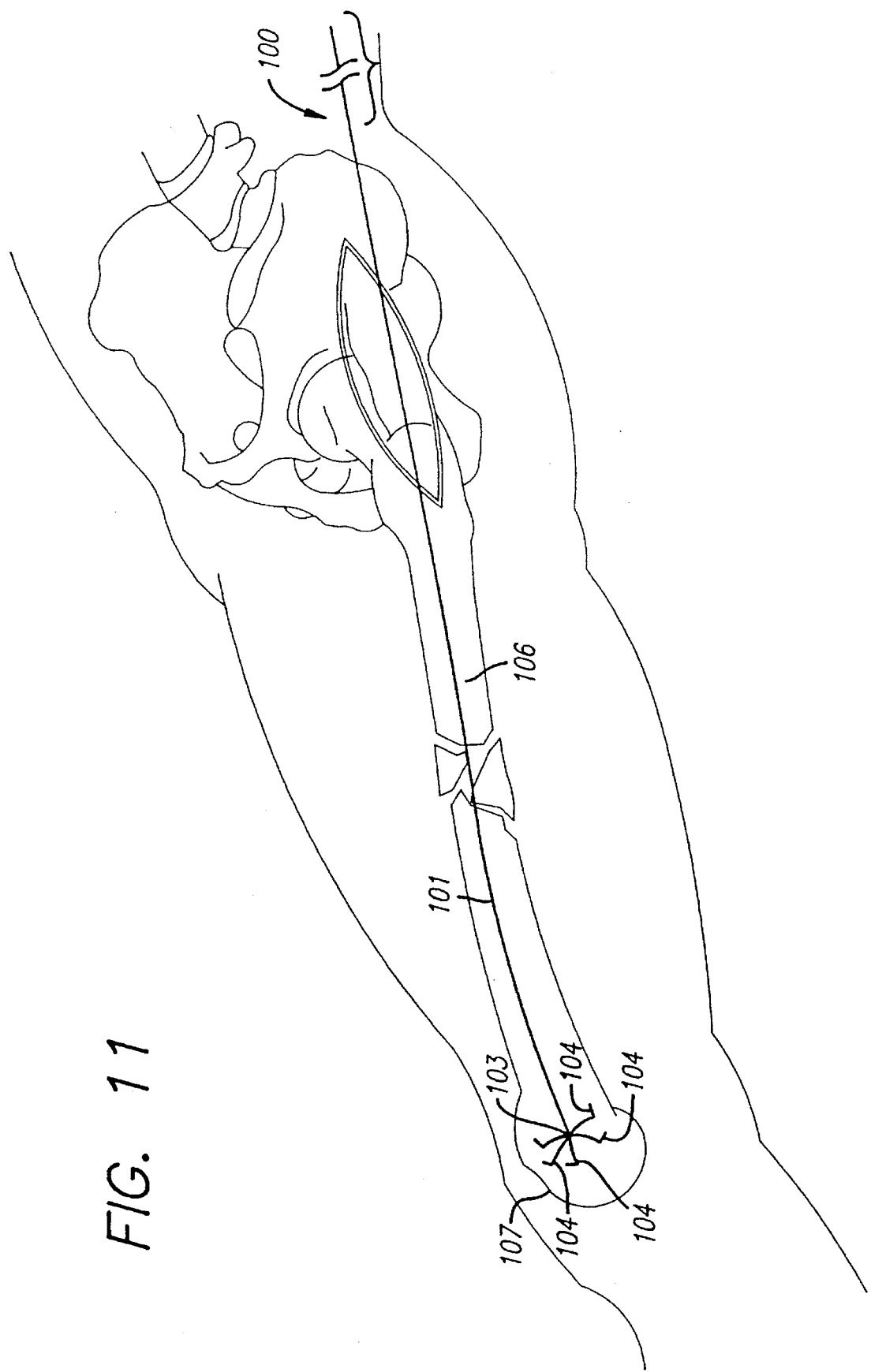
FIG. 11 illustrates the secured position of a guide rod in accordance with an embodiment of the present invention after retraction of the reaming instrument of FIG. 4.

Typically, there is little clearance between the guide rod 100 and the hollow of the reaming instrument 108, hence, advancement and retraction of the reaming instrument will often exert a force on the guide rod 100 due to contact of the inside surface of the hollow reaming rod 108 with the guide rod 100. However, since the finger members 104 of the retention mechanism 103 have anchored the guide rod 100 into place, such contact can be overcome without adversely effecting the guide rod's placement; the guide rod will remain in its desired location throughout the reaming operation as seen in FIG. 11.

Figure 12:
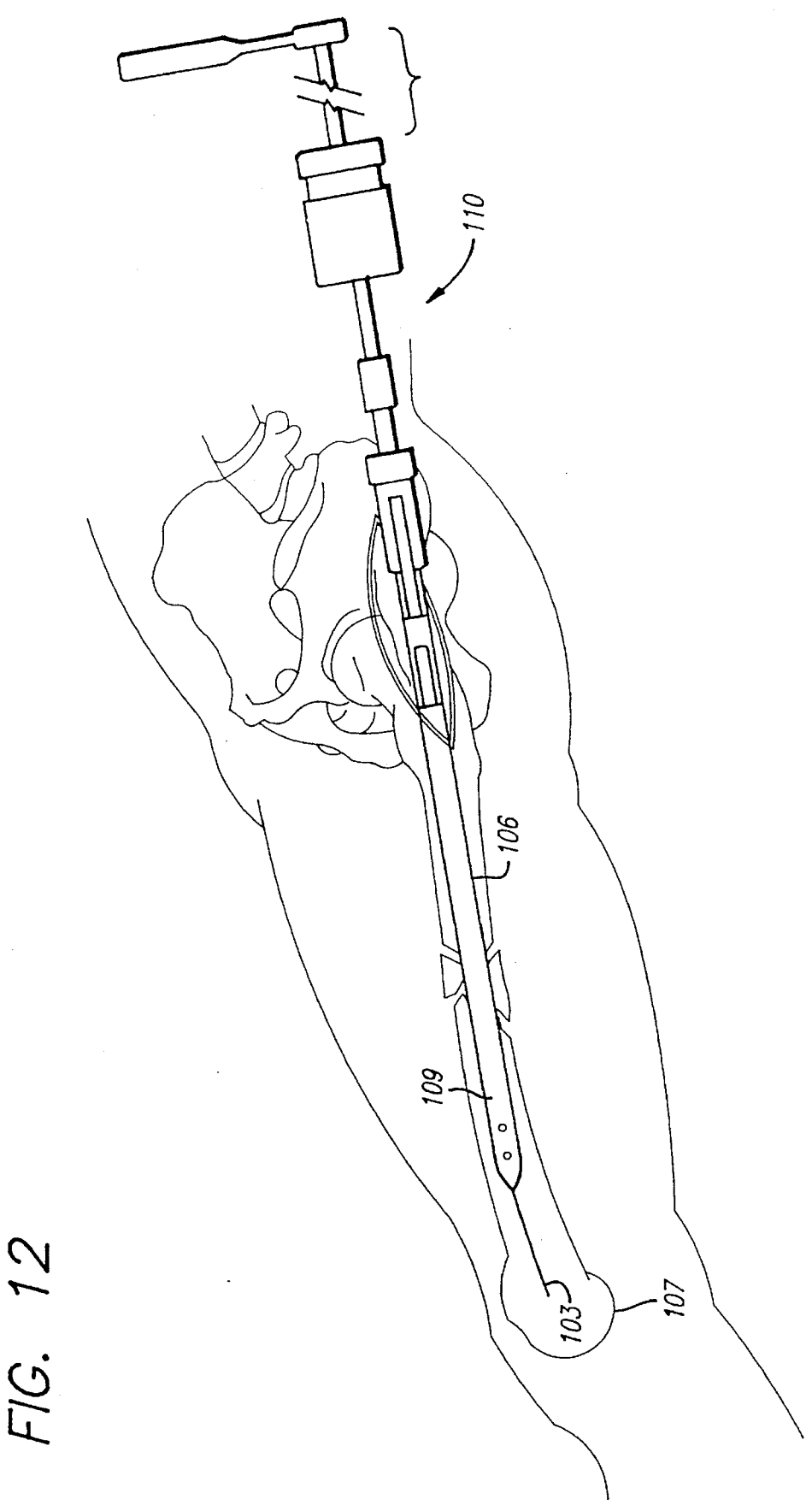
FIG. 12 illustrates the insertion of a permanent nail over a guide rod in accordance with an embodiment of the present invention and the configuration of the guide rod just prior to removal of the guide rod from the medullary canal of a fractured femur.

Once reaming has been completed, the medullary canal 106 is ready to receive the permanent nail 109 that will stabilize the fracture as depicted in FIG. 12. As with the reaming instruments, the nail 109 is hollow and therefore able to be guided into place by advancement over the guide rod 100 with a known mallet and nail alignment assembly 110. During insertion, the guide rod is prevented from any movement urged by contact between the nail 109 and the guide rod 100 because the guide rod is anchored into place by the finger members 104 of the retention mechanism.

Once the nail 109 has been advanced to its desired final position, the mallet and nail alignment assembly 110 is removed and the handle assembly 102 is remounted onto the guide rod 100. The retention mechanism 103 is unlocked and deactuated thus causing the flaring finger members 104 to return to their original position within the elongated rod section 101, out of contact with the material within the bone as depicted in FIG. 12. This, of course, also releases the guide rod 100 from its anchored position within the medullary canal 106. The guide rod is then removed from the medullary canal 106 leaving the nail 109 in place. Finally, the nail is secured to the bone with a known drilling and nailing procedure.

While the invention has been described with reference to a particular embodiment, it is understood that the embodiment is merely illustrative as there are numerous variations and modifications which may be made to those skilled in the art. Thus, the invention is to be construed as being limited only by the spirit and scope of the appended claims.

What is claimed is:

1. A guide rod assembly for reaming a medullary canal of a bone and for placement of a guide rod into said medullary canal comprising:

at lease one hollow reaming instrument;

an elongated rod having an external surface of a substantially constant diameter along its length, said substantially constant diameter being of a size smaller than the internal diameter of said at least one hollow reaming instrument so that said rod can serve as a guide for said at least one remaining instrument;

said elongated rod having a smoothly shaped distal end to facilitate movement of said elongated rod through bone material within an unreamed medullary canal of said bone during placement of said elongated rod in said canal;

a retention mechanism for holding said elongated rod in a desired position in said medullary canal during retraction of a hollow reaming instrument out of said medullary canal wherein said reaming instrument is being guided by said elongated rod during said retraction;

said retention mechanism including at least one member movable from a first position within said substantially constant diameter of said external surface to a second position outside said substantially constant diameter of said external surface such that said at least one member extends beyond said external surface of said elongated rod so as to come into contact with material in said bone and thereby hold said elongated rod in said desired position during retraction of said at least one reaming instrument;

said retention mechanism disposed at a distil end of said elongated rod; and, a removable handle situated at a proximal end of said elongated rod such that said elongated rod may receive said at least one reaming instrument when said handle is removed.

2. A guide rod assembly as set forth in claim 1, wherein said at least one member of said retention mechanism is a finger member that flares into contact with said material in said bone.

3. A guide rod assembly as set forth in claim 1, wherein said distal end of said elongated rod is bullet-shaped.

4. A guide rod assembly as set forth in claim 1, wherein said elongated rod is formed of a flexible material.

5. A guide rod assembly as set forth in claim 1, wherein said elongated rod includes a plurality of radiopaque measuring markers disposed at regular intervals along a length of said elongated rod.

6. A guide rod assembly as set forth in claim 1, wherein said retention mechanism includes a plurality of finger members and wherein said first position is a position in which said finger members are located within said elongated rod at said distal end and said second position is a position in which said finger members extend outside said elongated rod from said distal end.

7. A guide rod assembly for reaming a medullary canal of a bone and for placement of a guide rod into said medullary canal comprising:

at lease one hollow reaming instrument;

an elongated rod having an external surface of a substantially constant diameter along its length, said substantially constant diameter being of a size smaller than the internal diameter of said at least one hollow reaming instrument so that said rod can serve as a guide for said at least one remaining instrument;

said elongated rod having a smoothly shaped distal end to facilitate movement of said elongated rod through bone material within an unreamed medullary canal of said bone during placement of said elongated rod in said canal;

a retention mechanism for holding said elongated rod in a desired position in said medullary canal during retraction of a hollow reaming instrument out of said medullary canal wherein said reaming instrument is being guided by said elongated rod during said retraction;

said retention mechanism including at least one member movable from a first position within said substantially constant diameter of said external surface to a second position outside said substantially constant diameter of said external surface such that said at least one member extends beyond said external surface of said elongated rod so as to come into contact with material in said bone and thereby hold said elongated rod in said desired position during retraction of said at least one reaming instrument; and, said retention mechanism disposed at a distal end of said elongated rod.

8. A guide rod assembly as set forth in claim 7, wherein said at least one member of said retention mechanism is a finger member that flares into contact with said material in said bone.

9. A guide rod assembly as set forth in claim 7, wherein said distal end of said elongated rod is bullet-shaped.

10. A guide rod assembly as set forth in claim 7, wherein said elongated rod includes a plurality of radiopaque measuring markers disposed at regular intervals along a length of said elongated rod.

11. A guide rod assembly as set forth in claim 7, wherein said retention mechanism includes a plurality of finger members and wherein said first position is a position in which said finger members are located within said elongated rod at said distal end and said second position is a position in which said finger members extend outside said elongated rod from said distal end.

* * * * *